(12) United States Patent
Frandsen et al.

(10) Patent No.: US 8,304,047 B2
(45) Date of Patent: Nov. 6, 2012

(54) LAMINATED INSECTICIDE DISPENSER

(75) Inventors: Mikkel Vestergaard Frandsen, Kolding (DK); Ole Skovmand, Montpellier (FR)

(73) Assignee: Vestergaard Frandsen SA, Lausanne (CH)

( * ) Notice: Subject to any disclaimer, the term of this patent is extended or adjusted under 35 U.S.C. 154(b) by 1623 days.

(21) Appl. No.: 10/503,093

(22) PCT Filed: Jan. 30, 2003

(86) PCT No.: PCT/DK03/00055
§ 371 (c)(1),
(2), (4) Date: Oct. 4, 2004

(87) PCT Pub. No.: WO03/063587
PCT Pub. Date: Aug. 7, 2003

(65) Prior Publication Data
US 2005/0089657 A1 Apr. 28, 2005

(30) Foreign Application Priority Data
Jan. 31, 2002 (DK) ................................ 2002 00148

(51) Int. Cl.
*B32B 27/04* (2006.01)
*B32B 27/06* (2006.01)

(52) U.S. Cl. ................. 428/35.7; 428/34.1; 442/123

(58) Field of Classification Search .................. 428/34.1, 428/35.7; 442/123
See application file for complete search history.

(56) References Cited

U.S. PATENT DOCUMENTS

| | | | |
|---|---|---|---|
| 4,094,119 A * | 6/1978 | Sullivan | 53/400 |
| 4,198,782 A | 4/1980 | Kydonieus et al. | |
| 4,318,253 A * | 3/1982 | Wedel | 52/63 |
| 4,639,393 A | 1/1987 | Von Kohorn et al. | |
| 4,666,767 A * | 5/1987 | Von Kohorn et al. | 424/410 |
| 5,071,704 A | 12/1991 | Fischel-Ghodsian | |
| 5,750,129 A * | 5/1998 | Wakarchuk | 424/408 |
| 5,820,875 A * | 10/1998 | Fallon et al. | 424/448 |
| 5,902,598 A * | 5/1999 | Chen et al. | 424/423 |
| 6,096,814 A * | 8/2000 | Tamura et al. | 524/232 |
| 6,117,997 A * | 9/2000 | Bulliard et al. | 544/216 |
| 6,309,986 B1 | 10/2001 | Flashinski et al. | |
| 6,355,264 B1 * | 3/2002 | Garrison et al. | 424/405 |

FOREIGN PATENT DOCUMENTS

| | | |
|---|---|---|
| EP | 0 342 126 | 11/1989 |
| GB | 2 131 740 | 6/1984 |

* cited by examiner

*Primary Examiner* — Erik Kashnikow
(74) *Attorney, Agent, or Firm* — James Creighton Wray

(57) ABSTRACT

A laminated insecticide dispenser where a central layer contains an insecticide that migrates through the outer layer to the surface of the dispenser. The outer layer also comprises a UV protector which migrates to the surface in order to minimize the UV damage induced on the insecticide.

16 Claims, 1 Drawing Sheet

LAMINATED INSECTICIDE DISPENSER

Figure 1A:
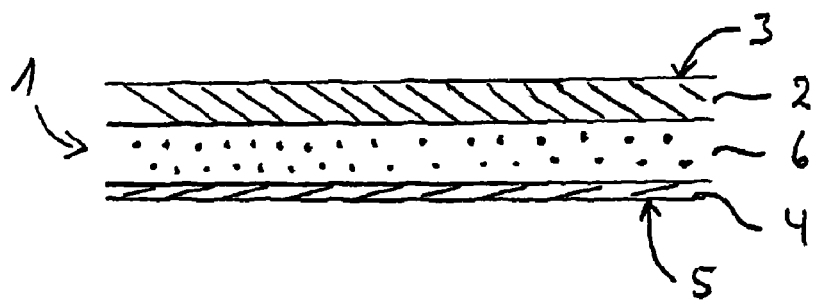

This application claims the benefit of Danish Application No. 2002 00148 filed Jan. 31, 2002 and PCT/DK03/00055 filed Jan. 30, 2003.

FIELD OF THE INVENTION

The present invention relates to a laminiated insecticide dispenser, for example a three layer tarpaulin.

BACKGROUND OF THE INVENTION

In order to control insects that may be harmful or otherwise undesirable to man, much attention has been directed to improvements in methods for delivering chemical pest control agents.

A special insecticide dispenser is known from U.S. Pat. No. 4,639,393 disclosing a laminated dispenser with two outer wall elements enclosing an inner layer containing a pest controlling agent. The pest controlling agent is able to migrate through the outer layers for a controlled release of the agent to the surface of the dispenser. Such a dispenser may be used for example for wall paper, floor coverings or tarpaulins.

It is well known that insecticides when exposed to ultra violet (UV radiation) are degraded through the UV induced chemical reactions. The dispenser disclosed in U.S. Pat. No. 4,639,393 takes into account UV protection of the pesticidal agent in the internal reservoir by incorporation of an ultra violet light screening agent in the wall portion of the dispenser.

However, the disclosure in U.S. Pat. No. 4,639,393 does not take into account any protection of the pest controlling agent after migration to the outer surface of the wall element Especially in tropic regions, UV radiation is very strong and the insecticide that has migrated to the surface of the laminate may disintegrate at a rate so high that no efficient insecticidal effect may be achieved. Therefore, the laminated dispenser disclosed in the above mentioned patent is primarily suited for indoor use or generally where high levels of UV radiation is avoided. In connection with applications where a high intensity of UV radiation is given, the insecticide release from a dispenser as disclosed in U.S. Pat. No. 4,639,393 has to be fast such that a suitable active level of insecticide, or alternatively an insect attractant, can be maintained on the surface. However, this limits the lifetime of the dispenser, because the insecticide reservoir is emptied after relatively short time, for example a few weeks.

It is the purpose of the invention to improve existing dispensers such that they are more suitable for application in outdoor environments where the dispenser is exposed to primarily high level UV radiation.

DESCRIPTION OF THE INVENTION

This purpose is achieved with a laminated insecticide dispenser comprising a first outer solid, non porous polymeric wall element with one side facing the environment of said dispenser and constituting a first surface of the dispenser, a second outer wall element with one side facing the environment of the dispenser and constituting a second surface of the dispenser, and at least one inner layer between the first and the second wall element. The inner layer comprises at least one pesticidal agent being capable of migration through the first outer wall element. The first outer wall element contains a UV protecting agent to reduce the UV radiation induced degradation of the pesticidal agent when the pesticidal agent is exposed to UV radiation. According to the invention, this UV protecting agent is capable of migrating through the first outer wall element for reaching the first surface.

The UV protective agent used in connection with the invention is capable of reducing the UV radiation induced degradation of the pesticidal substance, also when this pesticidal substance is on the first surface of the dispenser, such that the pesticidal substance may be optimally efficient as long as possible. Due to the reduced degradation of the pesticidal substance on the surface of the dispenser, a relatively small amount of pesticidal substance has to be supplied to the surface by migration through the outer wall element. Thus, by having a UV protecting agent supplied to the dispenser surface, the amount of used pesticides is reduced and the life time of the laminated insecticide dispenser according to the invention is prolonged as compared to laminated dispensers according to prior art.

The first outer wall element is constructed such that the migration speed of the pesticidal substance is fast enough to ensure an effective level of the pesticidal substance on the outer surface of the dispenser according to the invention. On the other hand, in order to avoid over shooting of the necessary effective level of the pesticidal substance, the migration rate through the first outer wall element may be controlled by migration moderation. Such moderation may be achieved by the physical properties of the outer wall element, for example the density or the thickness. However, the migration rate for the pesticidal substance may also be controlled by migration inhibitors on the inner surface of the first outer wall element or inside the first outer wall element.

In principle, the migration to the surface of the dispenser may also be reduced by a migration inhibitor on the surface of the dispenser. However, in this case, a large amount of the migrated pesticidal agent may accumulate on the inside of the wall element just below the migration inhibitor on the surface, which is inconvenient, as the UV intensity at this location is stronger than at the reservoir location inside the dispenser. Therefore this solution—though possible—is not preferred in connection with the invention. A better option is to have the migration inhibition layer on the inner side of the wall element or throughout the wall element. Hereby, the release rate from the inner layer to the surface becomes independent on the concentration in the inner layer, a so-called first order release rate, and becomes constant over long time.

Usable migration inhibitor are for example triazine derivatives, which at the same time have a fire resisting effect.

When a dispenser according to the invention is used immediately after production, some time may pass before the pesticide has migrated to the surface from the inner layer. In order to avoid a long initial period with a too low concentration of insecticide on the surface of the dispenser, pesticide may also be incorporated in the first outer wall element or even be disposed on the surface from the beginning. Such an initial application to the surface may be achieved, for example, by spraying on the surface.

A dispenser according to the invention may in a further development be constructed such that the release of the insecticide or the UV protecting agent or both is temperature dependent in a predetermined way. For example, if the dispenser is to be used in tropic regions, a relatively high temperature can be expected, when the dispenser is exposed to sun light. In contrast, the temperature during storage and transport is usually much lower. This fact can be utilized by a temperature dependent migration speed such that the relatively low temperature during storage and transportation results in a slow migration or even negligible migration of the UV protecting agent and/or the insecticide—allowing a long term storage of the dispenser according to the invention—whereas the migration speed is increased when the dispenser is exposed to sunlight or high temperature.

A temperature dependent release of the UV protecting agent is advantageous in tropical regions because extensive exposure to sunlight with corresponding heating of the dispenser also increases the need for a relatively high amount of UV protecting agent. This way, the dispenser according to the invention functions as a self-regulating dispenser of a UV protecting agent.

The migration rate of the UV protecting agent through the first outer wall element may as well be controlled by the physical properties of the sheet or by applying a migration inhibitor in the first outer wall element, where the inhibitor is directed towards a control of the migration rate of the UV protecting agent. This migration inhibitor may optionally function in dependency of the temperature of the dispenser.

The UV protecting agent is preferably incorporated in the first outer wall element, because it, this way, yields an efficient UV protection of the pesticide reservoir. Also, typically the migration speed is lower for UV protecting agents than for pesticidal agents, why the UV protecting agent preferably is located nearer to the dispenser surface from the beginning than the pesticidal agent itself, for example in the outer layer. In case that the migration speed of the UV protecting agent through the outer wall element is fast enough for the desired effect, the UV protecting agent may be supplied to the first outer sheet from a reservoir comprised by the inner layer.

By applying different migration inhibitors, where one inhibitor or one group of inhibitors are acting on the pesticidal substance and another inhibitor or group of inhibitors may act on the UV protecting agent, optimized migration rates may be achieved such that a perfectly match results between the amount of UV protecting agent and the pesticidal agent on the surface of the laminated insecticide dispenser according to the invention.

In case that the pesticidal agent according to the invention is a mixture of a number of pesticidal substances, different migration inhibitors may be applied, where each inhibitor is directed towards rate migration control of at least one of the substances. Also, the insecticides by themselves will have different migration rates, and this can be exploited for a successive release of insecticides. Equivalently, in case that the UV protecting agent consists of a number of UV protection substances, a number of special migration rate reducing inhibitors may be applied for controlling the migration rate of the individual UV protecting substances. As above, the different migration rates of different UV filters or other types of protecting substances can be used to match with insecticides with different absorption spectra or to obtain a prolonged UV protection by combining fast and slow migrating filters. The different types of migration inhibitors may be chosen with substantial temperature dependence matching certain appliances, for example use in tropical regions with strong exposure to sunlight.

Thus, it is possible according to the invention to achieve an optimum amount of different pesticidal substances on the surface of the dispenser and at the same time achieve an optimum amount of UV protection substances on the surface of the dispenser such that the insecticides may act as efficient as possible and for at time as long as possible. Dispensers according to the invention are intended to work efficiently for years.

A long lasting dispenser according to the invention is especially suitable for refugee camps in warm countries because the financial aid often is limited and irregular. Therefore, once a dispenser, for example as part of a tent, has been financed and delivered, the functioning of this dispenser should be as long as possible. The ready-to-use tent or tarpaulin further has the advantage that other insecticide handling in the camp is much reduced or avoided.

Possible migration inhibitors are metallic salts like bromides, which also may have some fire retardation effects. Substances as Carbon Black may be used as well, where Carbon Black has the additional property of being a UV protector. Substances as kaolin, stearates and migrating UV filters may, on the other hand, be used for increasing migration.

Optimization of the insect combating properties of the dispenser is furthermore achieved by matching the UV protecting agent or agents to the pesticidal agent in that the wavelength range for the most effective UV filter properties of the protecting agent overlaps with those wavelengths, where the pesticide is most sensitive for disintegration.

In order to prevent the polymer in the dispenser from UV induced disintegration, the different layers in the dispenser may contain additional UV protectors, for example Carbon Black, as far as the migrating UV protecting agent is not sufficiently effective.

Furthermore, the outer sheet layers and the inner layer may additionally contain HALS molecules. HALS is an abbreviation for Hindered Amine Light Stabilizers, which is a group of additives having a common chemical structure (a piperidine ring) as part of their molecule. These highly effective UV stabilizers protect the polymer by scavenging free radicals that may occur due to UV irradiation. The effect of Hals molecules is also beneficially on the UV protecting agent as it prolongs the lifetime of this agent.

The second outer wall element may be of the same kind as the first outer wall element and exhibit analogue properties for a likewise function. However, the second outer wall element may alternatively be of a different kind, for example it may be an element which completely blocks any migration of pesticides or UV protecting agents. An example of a blocking wall element is a metal foil.

Alternatively, the second outer wall element may be constructed such that it prevents the UV protecting agent to migrate through it, but permits the pesticidal agent to migrate through. The latter embodiment, may be used in cases where the dispenser is only exposed to UV radiation on the first side of the dispenser. This would for example be the case, if the laminated dispenser according to the invention is used as a roof or a tent, where the outer side, namely the first side of the dispenser is exposed to UV radiation, while the second side—for example being inside the tent—is not exposed to UV radiation. The total blocking of the migration of the UV protecting agent through the second outer wall element implies that only part of the amount of the UV protecting agent is necessary in such a dispenser as compared with a dispenser where the first and the second outer wall elements allow migration of the UV protecting agent, for example by being identical.

The second outer wall element may be different from the first outer wall element in that only some special pesticidal substances migrate through the first outer wall element, while other special pesticidal substances migrate through the second outer wall element. Likewise may apply for different UV protecting substances. This would be useful in case that a dispenser according to the invention is set up with one side facing the morning sun and the other side facing the evening sun. Insects that are active in the morning may set on the warm side of the dispenser, which is facing the morning sun, while other insects may be touching the other side of the dispenser which is facing the evening sun. For those insects that are active in the morning as compared to those that are active in the evening, different insecticides may be necessary, why a selective migration of pesticidal substances towards the first or the second side of the dispenser would be highly useful. Analogue arguments apply for the UV protecting substances that are related to the different pesticidal substances. Also, such considerations are advantageous, if the dispenser according to the invention is used as a tent, where insects inside the shady tent may primarily be of a different kind than insects on the sunny and warm outside surface of the tent.

The case that only some specific pesticides migrate through the first outer wall element while others migrate through the second outer element may be utilized for combat of insects that may readily become resistant to pesticides. If an insect has become resistant to the pesticide on one surface of the dispenser, there may still be a high chance of lethal effect on this insect from the pesticide on the other surface.

The migration speed of the different agents or substances may be regulated by physical properties as density and thickness of the outer wall elements as described above. Alternatively, the migration rate may be regulated through inclusion of different kinds of migration filters between the outer wall elements and the inner layer or by constructing an inner layer consisting of a compound structure of different inner wall elements and migration filters. Furthermore, the inner layers or outer wall elements may have different thickness and different migration rates for different pesticidal agent or UV protecting agents. Thus by arranging a suitable number of different inner layers and outer wall elements with different thickness, densities, applied migration filters, and chemical migration inhibitors and migration reducers, almost any desired combination of pesticidal agents and UV protecting agents are possible to obtain at the first and the second surface of the dispenser.

A number of substances used in an applicable pesticidal agents are mentioned in the following together with UV protecting agents.

The present invention relates to but is not limited to the following active insecticides selected from the group comprising pyrethroid compounds such as

- Etofenprox: 2-(4-ethoxyphenyl)-2-methylpropyl-3-phenoxybenzyl ether,
- Fenvalerate: (RS)-alpha-cyano-3-phenoxybenzyl(RS)-2-(4-chlorophenyl)-3methylbutyrate,
- Esfenvalerate: (S)-alpha-cyano-3-phenoxybenzyl(S)-2-(4-chlorophenyl)-3-methylbutyrate,
- Fenpropathrin: (RS)-alpha-cyano-3-phenoxybenzyl 2,2,3,3-tetramethylcyclopropanecarboxylate,
- Cypermethrin: (RS)-alpha-cyano-3-phenoxybenzyl (1RS)-cis, trans-3-(2,2-dichlorovinyl)-2,2-dimethylcyclopropanecarboxylate, and isomer variants as alfa- and beta-cypermethrin,
- Permethrin: 3-phenoxybenzyl (1RS)-cis,trans-3-(2,2-dichlorovinyl)-2,2-dimethyl-cyclopropanecarboxylate,
- Cyhalothrin: (RS)-alpha-cyano-3-phenoxybenzyl (Z)-(1RS)-cis-3-(2-chloro-3,3,3-trifluoroprop-1-enyl)-2,2-dimethylcyclopro panecarboxylate, and isomer variants as lambda-cyhalothrin,
- Deltamethrin: (S)-alpha-cyano-3-phenoxybenzyl (1R)-cis-3-(2,2-dibromovinyl)-2,2-dimethylcyclopropanecarboxylate,
- Cycloprothrin: (RS)-alpha-cyano-3-phenoxybenzyl (RS)-2,2-dichloro-1-(4-ethoxyphenyl)cyclopropanecarboxylate,
- Fluvalinate (alpha-cyano-3-phenoxybenzyl N-(2-chloro-alpha,alpha,alpha-trifluoro-p-tolyl)-D-valinate),
- Bifenthrin: (2-methylbiphenyl-3-ylmethyl)0(Z)-(1RS)-cis-3-(2-chloro-3,3,3-trifluoro-1-propenyl)-2,2-dimethylcyclopropanecarboxylate,
- 2-methyl-2-(4-bromodifluoromethoxyphenyl)propyl (3-phenoxybenzyl) ether,
- Silafluofen: 4-ethoxyphenyl (3-(4-fluoro-3-phenoxyphenyl)propyl}dimethylsilane,
- D-fenothrin: 3-phenoxybenzyl (1R)-cis,trans)-chrysanthernate,
- Cyphenothrin: (RS)-alpha-cyano-3-phenoxybenzyl (1R-cis, trans)-chrysanthemate, D-resmethrin: 5-benzyl-3-firylmethyl (1R-cis,trans)-chrysanthemate,
- Acrinathrin: (S)-alpha-cyano-3-phenoxybenzyl (1R-cis (Z))-(2,2-dimethyl-3-(oxo-3-(1,1,1,3,3,3-hexafluoropropyloxy)propenyl(cyclopropanecarboxylate,
- Cyfluthrin: (RS)-alpha-cyano-4-fluoro-3-phenoxybenzyl 3-(2,2-dichlorovinyl)-2,2-dimethylcyclopropanecarboxylate,
- Tefluthrin: 2,3,5,6-tetrafluoro-4-methylbenzyl (1RS-cis (Z))-3-(2-chloro-3,3,3-trifluoroprop-1-enyl)-2,2-dimethylcyclopropanecarbo xylate,
- Transfluthrin: 2,3,5,6-tetrafluorobenzyl (1R-trans)-3-(2,2-dichlorovinyl)-2,2-dimethylcyclopropanecarboxylate,
- Tetramethrin: 3,4,5,6-tetrahydrophthalimidomethyl (1RS)-cis, trans-chrysanthemate,
- Allethrin: (RS)-3-allyl-2-methyl-4-oxocyclopent-2-enyl (1RS)-cis, trans-chrysanthemate,
- Prallethrin: (S)-2-methyl-4-oxo-3-(2-propynyl)cyclopent-2-enyl (1R)-cis, trans-chrysanthemate,
- Empenthrin: (RS)-1-ethynyl-2-methyl-2-pentenyl (1R)-cis,trans-chrysanthemate,
- Imiprothrin: 2,5-dioxo-3-(prop-2-ynyl)imidazolidin-1-ylmethyl (1R)-cis, trans-2,2-dimethyl-3-(2-methyl-1-propenyl)-cyclopropanecarboxylate,
- D-flamethrin: 5-(2-propynyl)-furfuryl (1R)-cis,trans-chrysanthemate, and 5-(2-propynyl)furfuryl 2,2,3,3-tetramethylcyclopropanecarboxylate;

other active insecticides that may be used alone or in combination, but preferably not mixed with pyrethroids, are e.g. carbamate compounds such as

- Alanycarb: S-methyl-N[[N-methyl-N-[N-benzyl-N(2-ethoxy-carbonylethyl)aminothio]carbamoyl]thioacetimidate,
- Bendiocarb: 2,2-dimethyl-1,3-benzodioxol-4yl-methylcarbamate),
- Carbaryl (1-naphthyl N-methylcarbamate,
- Isoprocarb: 2-(1-methylethyl)phenyl methylcarbamate,
- Carbosulfan: 2,3dihydro-2,2-dimethyl-7-benzofuranyl [(dibutylamino)thio]methylcarbamate,
- Fenoxycarb: Ethyl[2-(4-phenoxyphenoxy)ethyl]carbamate,
- Indoxacarb: Methyl-7-chloro-2,3,4a,5-tetrahydro-2-[methoxycarbonyl (-4-trifluoromethoxyphenyl)]
- Propoxur: 2-isopropyloxyphenol methylcarbamate,
- Pirimicarb: 2-dimethylamino-5,6-dimethyl-4-pyrimidinyl-dimethylcarbamate,
- Thidiocarb: Dimethyl N,N'(thiobis((methylimino)carbonoyloxy)bisethanimidiothioate),
- Methomyl: S-methyl N-((methylcarbamoyl)oxy)thioacetamidate,
- Ethiofencarb: 2-((ethylthio)methyl)phenyl methylcarbamate,
- Fenothiocarb: S-(4-phenoxybutyl)-N,N-dimethyl thiocarbamate,
- Cartap: S,S'-(2-5dimethylamino)trimethylene)bis(thiocarbamate)hydrochloride, Fenobucarb: 2-sec-butylphenylmethyl carbamate,3,5-dimethylphenyl-methyl carbamate,
Xylylcarb: 3,4-dimethylphenylmethylcarbamate;
additionally, active insecticides such as organophosphorous compounds may be applied in accordance with the invention including compounds such as
Fenitrothion: O,O-dimethyl 0-(4-nitro-m-tolyl)phosphorothioate,
Diazinon: 0,0-diethyl-0-(2-isopropyl-6-methyl-4-pyrimidinyl)phosphorothioate,
Pyridaphenthion: 0-(1,6-dihydro-6-oxo-1-phenylpyrazidin-3-yl) 0,0-diethyl phosphorothioate,
Pirimiphos-Etyl: 0,0-diethyl 0-(2-(diethylamino)-6-methyl-pyrimidinyl)phosphorothioate,
Pirimiphos-Methyl: 0-[2-(diethylamino)-6-methyl-4pyrimidinyl]0,0-dimethyl phosphorothioate,
Etrimphos: 0-6-ethoxy-2-ethyl-pyrimidin-4-yl-0,0-dimethyl-phosphorothioate,
Fenthion: 0,0-dimethyl-0-[-3-methyl-4(methylthio)phenyl phosphorothioate,
Phoxim: 2-(diethoxyphosphinothoyloxyimino)-2-phenylacetonitrile,
Chlorpyrifos: 0,0-diethyl-0-(3,5,6-trichloro-2-pyrinyl) phosphorothioate,
Chlorpyriphos-methyl: 0,0-dimethyl 0-(3,5,6-trichloro-2-pyridinyl)phosphorothioate,
Cyanophos: 0,0-dimethyl 0-(4cyanophenyl)phosphorothioate,
Pyraclofos: (R,S)[4chlorophenyl)-pyrazol-4-yl]-0-ethyl-S-n-propyl phosphorothioate, Acephate: 0,S-dimethyl acetylphosphoroamidothioate,
Azamethiphos: S-(6-chloro-2,3-dihydro-oxo-1,3-oxazolo [4,5-b]pyridin-3-ylmethyl phosphorothioate,
Malathion: 0,0-dimethyl phosphorodithioate ester of diethyl mercaptosuccinate,
Temephos: (0,0'(thiodi-4-1-phenylene) 0,0,0,0-tetramethyl phosphorodithioate,
Dimethoate: ((0,0-dimethyl S-(n-methylcarbamoylmethyl)phosphorodithioate,
Formothion: S[2-formylmethylamino]-2-oxoethyl]-O,O-dimethyl phosphorodithioate,
Phenthoate: 0,0-dimethyl S-(alpha-ethoxycarbonylbenzyl)-phosphorodithioate;
in addition, especially for ticks and mites, the following insecticides and acaricides may be applied:
Neonicotioids as Acetamidiprid and Imidacloprid:
    1-(6-chloro-3-pyridylmethyl)-N-nitro-2-imidazolidinimine;
Pyridins as Pyriproxyfen: 2-[1-+methyl-2-(4-phenoxyphenoxy)ethoxyy]pyridine;
Pyrimidines as Pyremidifen
    5-chloro-N-(2,-[4-(2-ethoxyethyl)-2,3-dimethyl-phenoxy]-ethyl)6-ethylpyrimid in-4-amin
Quinazoline as Fenazaquin: 4-[[-(1,1-dimethylethyl)phenyl, pyrazoler and phenyl
Pyrazoles as Dihydropyrazole, Fipronile, Tebufenpyrad, and Fenpyroximate:
    1,1-dimethylethyl-4-[[[[(1,3-dimethyl-5-phenoxy-1H-pyrazol-4-yl)-methylene]ammo]oxy]methyl]benzoate]
Pyrazoner as Tebufenpyrad,
Carbonitrils as Vaniliprol,
Hydrazins as Tebufenozide,
Hydrazons,
Azomethins,
Diphenyls as Bifenazate;

furthermore active insecticides with a sterilising effect on adult mosquitoes and/or with a growth regulating effect may applied such as:
(alfa-4-(chloro-alpha-cyclopropylbenzylidenamino-oxy)-p-tolyl)-3-(2,6-diflourobenzoyl)urea,
Diflubenzuron: N-(((3,5-dichloro-4-(1,1,2,2-tetraflouroethoxy)phenylamino)carbonyl)2,6 diflouro benzamid,
Triflumuron: 2-Chloro-N-(((4-(triflouromethoxy)phenyl)-amino-)carbonyl)benzamide, or
a triazin such as N-cyclopropyl-1,3,5-triazine-2,4,6-triamin.
Other possible agents are mentioned in U.S. Pat. No. 4,639,393.
The insecticidal agent may also contain an insect repellant, for example for repellant of certain predetermined insects.
The repellant is at least one from the group consisting of
N,N-Diethyl-meta-toluamide(DEET),
N,N-diethylphenylacetamide (DEPA),
1-(3-cyclohexen-1-yl-carbonyl)-2-methylpiperine,
(2-hydroxymethylcyclohexyl)acetic acid lactone,
(2-ethyl-1,3-hexandiol), indalone,
Methylneodecanamide (MNDA),
a pyrethroid not used for insect control such as (±)-3-allyl-2-methyl-oxocylopent-2-(+)enyl-(+)trans-chrysantemate(Esbiothrin),
a repellant derived from or identical with plant extracts like limonen, citronella, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella).
Instead of a repellent, a pest attractant may be used for attracting certain insects, for example certain pheromones. This way, the dispenser may be used for selective combat of specific species. For example some certain insects may be repelled while others may be attracted.
Also incorporated in the first and/or second outer wall element, or in the inner layer with migration through the outer wall elements, may be so called chemical arrestants. These are chemical substances that work through contact with insects such that insects stay longer at the exposed surface of the dispenser than they else would do. The longer stay of the insect on the surface of the dispenser may result in a more efficient combat with a higher kill rate. In order to prevent disintegration of the chemical arrestant, UV protecting agents may be employed for this as well.
Interesting as a UV protecting agent are Benzophenon-derivatives, for example the agent known under the commercial name Chimassorb 81, comprising the chemical substance Methanone,2-hydroxy4-(octyloxy)-phenyl. Chimassorb 81 is a UV protecting agent having an absorption in that part of the radiation spectrum, where deltamethrin and other pyrethroids absorb UV energy and get unstable. Because the molecules of Chimassorb 81 are rather small, it easily can diffuse through polyethylene, where polyethylene is a suitable polymer for the outer wall elements of the dispenser and optionally also for the inner layer. The diffusion ability for Chimassorb 81 through polymer is opposite to most others UV protecting agents, for which the diffusion speed is extremely low, especially those UV protecting substances that are used for UV protection of polyethylene.
Another suitable UV protecting agent is available from Ciba Geigy and known by the commercial name Tinuvin 326 containing the chemical substance with the name Phenol, 2-(5-chloro-2H-benzotriazole-2-yl)-6-(1,1-dimethyl)-4-methyl. Tinuvin 326 may be used for protection of polyethylene in which it does not migrate.

Chimasorb 81 as well as Tinuvin 326 have been observed to have a migration promoting effect.

Advantageously, Tinuvin 326 may be used in combination with Chimassorb 81. This has been demonstrated in an experiment, where the content of deltamethrin in a wall element was measured after UV radiation exposure. The measured results are shown in the table below.

| agent - start amount 1.3 | amount left after 16 hours | amount left after 24 hours |
|---|---|---|
| none | 0.34 | 0.18 |
| Chimasorb 81 | 0.89 | 0.71 |
| Tinuvin 326 | 0.44 | 0.40 |
| Tinuvin 326 + Chimasorb 81 | 1.03 | 0.87 |

The initial amount in the wall element was 1.3 g deltamethrin per kg wall element. It is clearly seen from the data in the table that a combination is an advantage as the amount of deltamethrin left after 24 hours is almost five times higher than without UV protecting agent.

Another suitable radical scavenger that may be used in connection with the invention is known under the commercial name Tinuvin 494™ available from Ciba Geigy®. It contains the high molecular stabilizer also known under the commercial name Chimasorb 119FL™. It contains 1,3,5-Triazine-2,4,6-triamin,N,N'''[1,2-ethane-diyl-bis, {[[4,6-bis[butyl(1,2,2,6,6-pentamethyl-4-piperidinyl]1-3,5-triazine-2-yl]imino]-3,1-propranediyl]}-bis[N',N''-dibutyl-N',N''-bis(1,2,2,6,6-pentamethyl -4-piperidinyl).

For most applications, the laminated dispenser according to the invention will be of flexible type for use as tents, shelters, tarpaulins, floor coverings or wall coverings. However, it is also possible that a laminate dispenser according to the invention is of the rigid type.

The inner layer may be a polymeric wall element of the porous and unporous type, but it may also be fabric or paper material that is soaked with a gel or a liquid. Alternatively, the inner layer may simply consist of a gel that is disposed between the outer wall elements.

A suitable material for the wall elements and the inner layer is polyethylene. However, as the extrusion temperature when producing polyethylene structures is so high that contained insecticides may disintegrate if contained in the structure. Therefore for certain pesticidal agents, PVC (poly vinyl chloride) may be preferred with an extrusion temperature of only 80-100° C. Further alternatives are for example nylon and soft polystyrene. The polyethylene may also contain EVA (ethylene-co-vinylacetate) and thus obtain a higher migration rates and a softer product.

A dispenser according to the invention may in addition comprise other substances that are useful in dependence of the actual application. For example, the dispenser according to the invention may in addition dispense smelling substances such that the dispenser or the region around the dispenser has an intended smell, for example a smell with a refreshing effect to human beings as peppermint oil, lemon oil or tea tree oil, or a smell which repels certain animals, for example tea tree oil for repelling fleas. This may be of advantage when a dispenser according to the invention is used as tarpaulin, for example in connection with tents for life aid or field hospitals. In this case, it may in addition be of advantage to use other substances, that may be used for repelling larger animals, for example cats or dogs or other kinds of predators—such kinds of substances are widespread commercially available in liquid form. For example, repellents to repel cats may include allyl isothiocyanate (oil of mustard), amyl acetate, anethole, capsaicin, cinnemaldehyde, citral, citronella, citrus oil, eucalyptus oil, geranium oil, lavender oil, lemongrass oil, menthol, methyl nonyl ketone, methyl salicylate, naphthalene, nicotine, paradichlorobenzene and thymol. A number of these substances are known to have refreshing effects on humans and pain relieving effect.

Other releasable substances from the dispenser according to the invention may be agents that have a medical effect, for example evaporating euphoriant or pain reducing substances, for example drugs, to be used in connection with wall elements, for example tents, around humans that are suffering of pain or different kinds of illness. Such kind of application may be considered in connection with warfare or during life aid in regions with catastrophes.

Another application of a dispenser according to the invention is as a direct cover to resting humans, where the dispenser may prevent nuisance due to insect attack. In this case, it can be of advantage if only the first surface of the dispenser facing away from the body is dispensing an insecticide, eventually in combination with an insect repellant. Optionally, the second surface, facing the human body may be dispensing a medical drug or a smelling agent as described above. A suitable smelling agent may be based on ethereal oils. Ethereal oils are known to have pain relieving and/or refreshing effects, for example orange oil, basil oil and peppermint oil.

As a further application, a dispenser according to the invention may form part of a wound cover, where the first surface forms the outer side of the wound cover and dispenses a pesticide, preferably with an insect repellant, and thus reduces the danger of infections due to insects, which is of pronounced risk in tropical countries. Facing the wound, the second surface of the dispenser may release a substance promoting the healing of the wound, for example including a bactericide and antioxidants. In this connection, it should be mentioned that tea tree oil is known to have antibacterial and fungicidal properties in addition to insect repelling effects.

SHORT DESCRIPTION OF THE DRAWING

The invention will be explained in more detail in the following with reference to the drawings, where FIG. 1 is a schematic of a dispenser according to the invention, FIG. 2 is a schematic of a compound dispenser structure.

DETAILED DESCRIPTION OF THE INVENTION

FIG. 1*a* shows a dispenser 1 according to the invention having a first outer solid, non porous polymeric sheet 2 constituting a first surface 3 of the dispenser 1. The dispenser penser 1 also has a second outer wall element 4 with one side constituting a second surface 5 of the dispenser 1. Between the first 2 and the second 4 outer wall element, an inner layer 6 is located. The thickness of the wall elements 2, 4 and the inner layer 6 may be mutually different, for example in dependence of the desired physical properties and functions.

Though shown as a flat sheet in FIG. 1*a*, the dispenser 1 according to the invention may as well have different shapes, for example bent, twisted, elliptical or round as shown in FIG. 1*b*. In case that the first 2 and the second 4 wall element are identical for the shown round embodiment, the inner layer 6 may in practice be surrounded by only one wall element substituting the first 2 and the second wall element 4.

In case that a dispenser as shown in FIG. 1*b* is fabricated with a small diameter, it may be used as a fiber that can be woven into other more complex structures, for example fabrics for clothes, or net structures.

The materials for the dispenser wall elements and the inner layer may be polyethylene, for example of low density type for the wall elements and of high density type for the inner layer. Also PVC may be used.

When using a dispenser according to the invention against mosquitoes, deltamethrin may be used as one of the migrating pesticidal agents. Different doses in the wall elements and the inner layer may be applied according to the preferred properties. In the following a few examples are given for possible doses, the doses, however, in no way being limiting the general aspects of the invention.

The surface dose of deltamethrin may be between 15 mg/m$^2$ and 150 mg/m$^2$, for example 100 mg/m$^2$. Experiments have shown that a dose of 1 g of deltamethrin per kg wall element can be used in an outer polyethylene wall element when the thickness of the wall element is 0.05 mm. The dose in the inner layer, which supplies the pesticidal agent to a low density polyethylene wall element for migration, is for example 6 g/kg when the thickness of the wall element is 0.1 mm.

As compared to deltamethrin, the necessary dose for etofenprox and permethrin is an order of magnitude higher, while the dose for malathion is about 20 times higher.

Figure 1B:
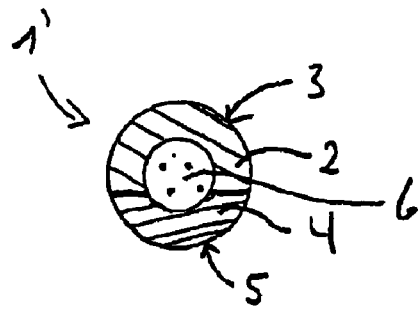

For a cylindrical dispenser as shown in FIG 1b, when used as a relatively thin fiber, the migration distance from the inner layer 6 to the surface 3 of the dispenser 1 is relatively short and the dose of migrating deltamethrin in the wall element 2, 4, may be chosen to for example 50 mg/m$^2$. This dose is dependent on the migration speed, which may be regulated with migration inhibitors in relation to the dose in the inner layer 6 which provides the insecticide for migration through the outer wall element 2,4.

For polyethylene, the content of pesticides normally is below 10% of the weight of polyethylene itself, as the pesticides influences the physical properties of the polyethylene for higher doses.

Figure 2:
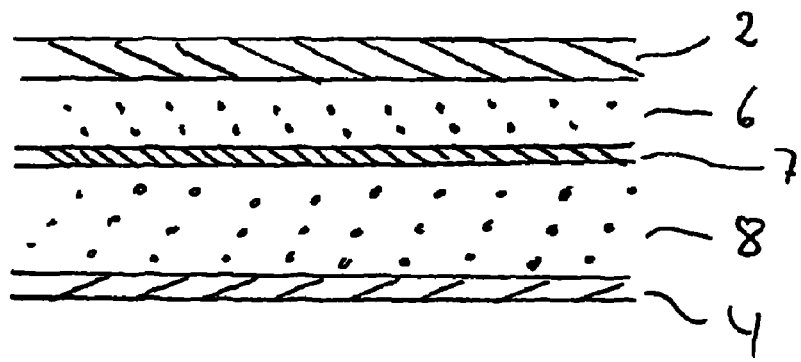

In FIG. 2, an alternative embodiment is shown, where in addition to the first 2 and the second 4 outer wall elements and the inner layer 6, also additional layers 7, 8 are incorporated in the dispenser 1. These additional layers 7, 8 may serve different purposes for the functioning of the dispenser 1.

For example, one additional layer 7 may separate the inner layer 2 from a further inner layer 8 such that the inner layer 6 feeds the first outer wall element 2 with one insecticide while the further inner layer 8 feeds the second outer wall element 4 with a different insecticide, a releasable medical drug, a smelling agent, or some other of the aforementioned substances. In order not to mix the substances in the inner layer 6 and further inner layer 8, they are separated by the separating additional layer 7.

The separating additional layer 7 may also be constructed such that certain substances are diffusing through the layer, while others are not. By choosing a multi layer principle with different thickness and diffusion/migration properties, a large variety of insecticides and UV protectors may be controlled with respect to the migration speed and with respect to which surface 3, 5 the insecticides are migrating to.

Apart from application as fibers in woven or non-woven structures, for example fabrics or nettings, and as tarpaulin or tents as described above, a dispenser according to the invention may be used for collars for animals, for example dogs and cats, or for ear tags on animals, for example cattle.

Furthermore, a dispenser according to the invention may be used as part of a building construction in order to prevent termite attack, for example as a covering of walls.

The invention claimed is:

1. A laminated insecticide dispenser comprising
a first outer solid, non porous polymeric wall element with one side facing the environment of said dispenser and constituting a first surface of said dispenser,
optionally a second outer wall element with one side facing the environment of said dispenser and constituting a second surface of said dispenser,
at least one inner layer between said first and second outer wall element or at least one inner layer surrounded by the first layer,
said inner layer comprising at least one pesticidal agent being capable of migration through said first outer wall element,
said first outer wall element containing a UV protecting agent, where said UV protecting agent reduces the UV radiation induced degradation of said pesticidal agent when said pesticidal agent is exposed to UV radiation
wherein said UV protecting agent is capable of migrating through said first outer wall element for reaching said first surface and wherein the migration speed of the UV protecting agent is fast enough to ensure UV protection on the first surface.

2. A laminated insecticide dispenser according to claim 1, wherein said first outer wall element comprises a migration inhibitor for reducing the migration speed of the pesticidal agent to the first surface of the dispenser.

3. A laminated insecticide dispenser according to claim 1, wherein said inner layer is at least one from the group consisting of
a porous or non-porous polymeric wall element,
a gel soaked or liquids soaked fabric,
a gel soaked or liquids soaked paper material,
a gel.

4. A laminated insecticide dispenser according to claim 1, wherein said inner layer constitutes a reservoir for at least one UV protecting agent capable of migrating through said first outer wall element and optionally through said second outer wall element.

5. A laminated insecticide dispenser according to claim 1, wherein said second outer wall element is at least one from the group consisting of
a wall element identical to said first wall element,
a wall element blocking the migration of the pesticidal agent,
a wall element blocking the migration of the UV protecting agent,
a non porous polymeric sheet,
a metal foil.

6. A laminated insecticide dispenser according to claim 1, wherein a HALS chemical is contained in at least one from the group comprising said inner layer, said first outer wall element and the second outer wall element.

7. A laminated insecticide dispenser according to claim 1, wherein said inner layer comprises a further pesticidal agent that is able to migrate through said second outer wall element but not through said first outer wall element.

8. A laminated insecticide dispenser according to claim 1, wherein said pesticidal agent contains at least one from group consisting of an insecticide, an insect repellant, an insect attractant, a bactericide, a fungicide.

9. A laminated insecticide dispenser according to claim 1, wherein said dispenser also comprises at least one from the following substances, an insect arrestant, a fire retarding agent, an animal repellant, a smelling agent, an ethereal oil, a medical drug, a euphoriant substance, a pain reducing substance.

10. A method of using a laminated insecticide dispenser according to claim 1 as a direct cover for humans comprising dispensing an insecticide only from the first surface of the dispenser facing away from a body.

11. A method of using a laminated insecticide dispenser according to claim 1 as a wall material for tents, comprising forming a tent from the dispenser.

12. A method of using a laminated insecticide dispenser according to claim 1 as a wall material for field hospitals, comprising forming a field hospital covering from the dispenser.

13. A method of using a laminated insecticide dispenser according to claim 1 as a wound cover, comprising dispensing an insecticide only from the first surface of the dispenser facing away from a body.

14. A method of using a laminated insecticide dispenser according to claim 1 as a collar for animals, comprising forming a collar from the dispenser.

15. A method of using a laminated insecticide dispenser according to claim 1 as an ear tag for animals, comprising forming an ear tag from the dispenser.

16. A method of using a laminated insecticide dispenser according to claim 1 as fibre material for woven or non-woven structures, comprising forming part of a woven or non-woven structure from said dispenser.

* * * * *